US005841510A

United States Patent [19]
Roggy

[11] Patent Number: 5,841,510
[45] Date of Patent: Nov. 24, 1998

[54] ROTATABLE DIAGNOSTIC LENS FOR EVALUATION OF THE IRIDO-CORNEAL ANGLE, RETINA AND OTHER PORTIONS OF THE EYE

[76] Inventor: David L. Roggy, 1409 Criterion Ave., St. Louis, Mo. 63138

[21] Appl. No.: 22,214

[22] Filed: Feb. 11, 1998

[51] Int. Cl.$^6$ ..................................................... A61B 3/13
[52] U.S. Cl. ............................................................. 351/218
[58] Field of Search ................................. 351/216, 217, 351/218, 219, 220, 221, 205, 200

[56] References Cited

U.S. PATENT DOCUMENTS

| | | | |
|---|---|---|---|
| 4,033,679 | 7/1977 | Sussman | 351/16 |
| 4,065,208 | 12/1977 | Currey | 351/6 |
| 4,568,157 | 2/1986 | Kurwa | 351/160 R |
| 5,252,025 | 10/1993 | Volk | 351/205 |
| 5,479,222 | 12/1995 | Volk | 351/219 |
| 5,537,164 | 7/1996 | Smith | 351/219 |
| 5,589,896 | 12/1996 | Mainster et al. | 351/219 |
| 5,654,639 | 8/1997 | Patel et al. | 351/205 |

OTHER PUBLICATIONS

Brochure of Ocular Instruments, Inc. entitled *Three Mirror Universal Lens*.
Brochure of Ocular Pathology Laboratory II entitled *Retinal Evaluation Utilizing The Three Mirror Fundus Contact Lens*.

Primary Examiner—George Manuel
Attorney, Agent, or Firm—Haverstock, Garrett & Roberts

[57] ABSTRACT

A lens device for examining portions of the human eye comprising inner and outer members each having opposed end portions, the outer member having a viewing lens adjacent one end portion thereof, the inner member being rotatably mountable within the outer member and having at least one mirror associated therewith, the at least one mirror being located adjacent the viewing lens when the inner member is positioned within the outer member, the inner member being rotatably movable relative to the outer member such that the at least one mirror can be selectively positioned relative to the viewing lens so that the appropriate area of the eye can be examined. Preferably, the inner member is rotatable a full 360° while the outer member remains stationary adjacent a patient's eye and, preferably, the inner member includes a plurality of circumferentially spaced mirrors. Although the present device is particularly adaptable for use in association with a wide variety of diagnostic lens such as gonioscopy and/or fundoscopic lens, the present device is likewise equally adaptable for use in many other eye lens applications including lenses used in laser treatment and/or surgery of the eye.

23 Claims, 3 Drawing Sheets

5,841,510

ROTATABLE DIAGNOSTIC LENS FOR EVALUATION OF THE IRIDO-CORNEAL ANGLE, RETINA AND OTHER PORTIONS OF THE EYE

FIELD OF THE INVENTION

The present invention relates generally to diagnostic lens devices for examining portions of the human eye and, more particularly, to a rotatable diagnostic lens housing any number of mirrors such as a gonioscopy lens or a fundus contact lens used for both irido-corneal and retinal evaluation as well as evaluation of other portions of the eye wherein the mirror/mirrors associated with the lens device are selectively rotatable to properly position the appropriate mirror opposite the area of the eye to be examined while the lens device remains stationary adjacent a patient's eye.

BACKGROUND OF THE INVENTION

Diagnostic lenses such as fundoscopic and gonioscopy lenses are commonly used for various types of ocular evaluation. These types of lenses are specifically designed to allow different areas of the retina and other portions of the eye to be evaluated and are typically used to review the posterior, equatorial and anterior areas of the retina, the ora serrata, the anterior chamber, the posterior chamber, the vitreous chamber, and more. Such lenses are useful because they allow an optometrist, ophthalmologist, or other eye care professional to examine the interior of the eye for potential ocular defects and/or disease. Because the pupil of the eye is small and the eye is essentially spherical, it is difficult to visually examine various interior portions of the eye with a normal lens. Thus, it is difficult to examine many portions of the eye such as peripheral portions of the vitreous chamber and the retina. In order to allow viewing of substantially the entire vitreous chamber and retina of the eye, as well as other areas, diagnostic lenses such as gonioscopy lenses and fundus contact lenses were developed.

Known prior art diagnostic lenses, such as the known gonioscopy lenses and multi-mirrored fundus contact lenses, typically include a concave central lens located at one end portion thereof and a plurality of mirrors positioned around the central lens which are encased in a funnel-shaped cone and protected by a planar glass viewing surface. The central viewing lens is utilized to assess the posterior 30° of the retina. Lateral or adjacent to the central lens are a plurality of mirrors, typically three mirrors, which are spaced 120° apart and are mounted at different angles of inclination to the funnel-shaped cone to allow different areas of the eye to be evaluated. Typically, these mirrors are angled at 59°, 67° and 73°. These mirrors reflect light at different angles so that different parts of the eye can be examined. In order to identify a specific mirror, manufacturers of these lenses have universally assigned three sizes and shapes to the mirrors so that the users thereof can quickly and easily identify each mirror and its associated angular inclination.

The selection and position of the specific mirror to be utilized during an evaluation depends upon that portion of the eye which needs to be evaluated. The selected mirror is then placed opposite the area to be evaluated. For example, if the 12 o'clock position of the peripheral retina needs to be evaluated, the median sized mirror which is angled at 67° can be positioned at the 6 o'clock position of the retina so as to view the affected area. Each mirror allows the user to inspect and evaluate different portions of the eye based upon the shape and inclination of such mirrors.

Because the mirrors are inclined at different angles and are typically circumferentially spaced apart, it is necessary to rotate the known prior art lenses a full 360° in order to examine the entire retina or other portions of the eye. Manipulation and positioning of the appropriate mirror at the appropriate location relative to the retina is generally accomplished by manually rotating the entire lens device on the eye of the patient until the selected mirror is located in the proper position. This orientation is obtained by simply rotating the lens between the forefinger and thumb of the user so that the lens is 180° opposite the area to be evaluated. Rotation of the lens can be accomplished with one or two hands depending upon the practitioner. The user, when using a prior art lens of this type, must therefore coordinate the use and manipulation of the slit-lamp biomicroscope which is used in conjunction with these types of lenses with manual rotation of the gonioscopy or other diagnostic lens on the eye of the patient. Although the affected eye is generally anesthetized and a cushioning agent is used between the eye and the central lens, some discomfort or even pain is normally experienced by the patient when the overall lens device is rotated into proper position. This rotation can also allow air bubbles to form in the cushioning agent or coupling fluid used between the eye and the central lens which can interfere with the examination and photographing of the patient's eye.

It is therefore desirable to provide a lens device which enables a user to freely manipulate the mirrors associated therewith without having to manually rotate the entire lens device on the patient's eye in order to properly orient the appropriate mirror for evaluation purposes.

SUMMARY OF THE INVENTION

The present invention teaches the construction and operation of several embodiments of a rotatable diagnostic lens for ocular evaluation wherein any number of mirrors associated with the present lens devices can be rotated separate and apart from the overall device so as to allow a user to view nearly all portions of the retina and other portions of the eye without likewise rotating the device on the patient's eye. The housing of the present devices are generally comprised of a pair of members, namely, an outer stationary member and an inner rotatable member, the inner member including at least one mirror which is selectively rotatable relative to the outer member. This arrangement enables the outer member to remain in a fixed stationary position adjacent a patient's eye while the inner member is selectively rotated to properly orient the appropriate mirror/mirrors for viewing of the desired area of the eye. The inner member can be rotated a full 360° allowing continuous or uninterrupted viewing of the interior portions of the eye without asserting additional pressure or causing additional discomfort or pain to the patient being evaluated. The present lens devices also enable a user to apply a constant pressure against the patient's eye during rotation of the inner member thereby substantially reducing or completely obviating any formation of air bubbles within the cushioning agent.

The present devices preferably include an outer funnel-shaped member having a concave central viewing lens associated with one end portion thereof and, importantly, an inner preferably funnel-shaped rotatable member to which any number of mirrors are preferably mounted at different angles of inclination similar to the mirrors associated with known fundoscopic or gonioscopy lenses. This inner rotatable member is integrally formed with or otherwise attached to an annular peripheral member whereby rotation of this annular peripheral member will likewise rotate the inner member to which the mirror/mirrors are mounted. Rotation of the annular peripheral member will therefore rotate the mirror/mirrors associated with the present devices without physically moving or manipulating the outer member as the present devices rest against the eye of the patient. The eye practitioner can therefore simply rotate the annular peripheral member using only the forefinger so that the selected mirror can be positioned opposite the area of the eye to be evaluated without physically moving the overall lens device against the eye of the patient. This substantially reduces or completely eliminates any discomfort to the patient which would normally take place during the mirror selection and positioning process. This rotation can be easily accomplished with one hand.

It is recognized and anticipated that a wide variety of different constructions can be utilized to rotatably mount the inner member in proper position within the stationary outer member. In this regard, it is preferred that the inner rotating member being integrally formed with the annular peripheral member and that such one-piece member be held in proper rotating position within the outer member through the use of any one of a plurality of different cooperatively engageable annular channel/projection arrangements. In one embodiment of the present invention, an annular channel formed by the annular peripheral member associated with the inner member cooperatively engages a corresponding annular lip or flange portion associated with the outer member, the annular peripheral member including a shoulder portion which mates with and cooperatively engages a corresponding shoulder portion associated with the annular flange portion of the outer member. It is also recognized and anticipated that a wide variety of other male/female connector arrangements may also be utilized in this particular application and still other mechanical arrangements are likewise possible to hold the inner rotating member in proper position within the outer member. Regardless of the specific mechanical construction, the mirror/mirrors associated with the present lens devices are selectively rotatable relative to the fixed central lens by simply rotating the annular peripheral member, a feature not possible with the known prior art diagnostic type lenses.

Although the present invention is particularly adaptable for use in association with a wide variety of diagnostic lenses such as gonioscopy and/or fundus contact type lenses, the present invention is likewise equally adaptable for use in many other eye lens applications including other types of ophthalmological lenses, as well as lenses used in laser treatment and/or surgery of the eye.

It is therefore an object of the present invention to provide a diagnostic and/or treatment lens device having at least one mirror associated therewith which is selectively rotatable to view different portions of the eye without moving that portion of the lens device positioned adjacent the patient's eye.

Other objects and advantages of the present invention will become apparent to those skilled in the art after considering the following detailed specification which discloses several representative embodiments of the present lens device in conjunction with the accompanying drawings wherein:

DETAILED DESCRIPTION OF THE INVENTION

Figure 1:
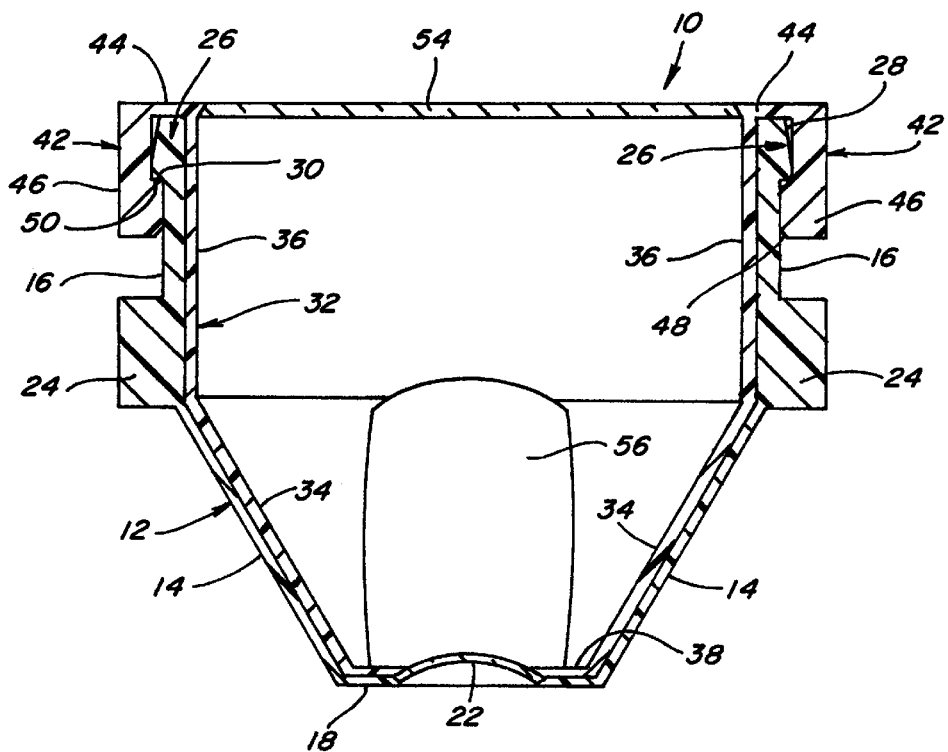
FIG. 1 is a cross-sectional view of one embodiment of the present lens device taken along line 1—1 of FIG. 2.
Figure 2:
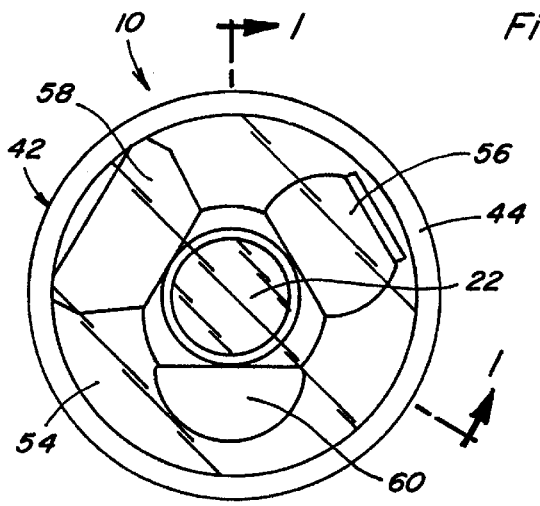
FIG. 2 is a top plan view of the lens device of FIG. 1 showing the fixed central viewing lens and three mirrors located adjacent thereto in association with the inner rotatable member.
Figure 3:
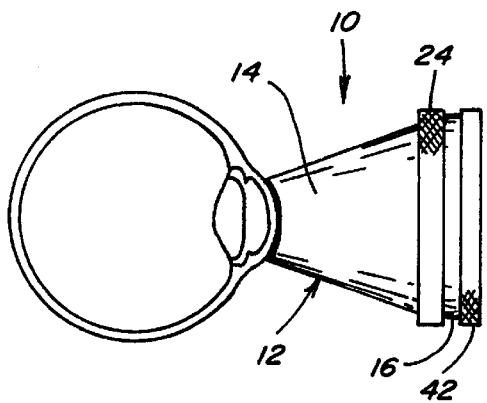
FIG. 3 is a side elevational view of the lens device of FIGS. 1 and 2 positioned for operative use adjacent a human eye.
Figure 5:
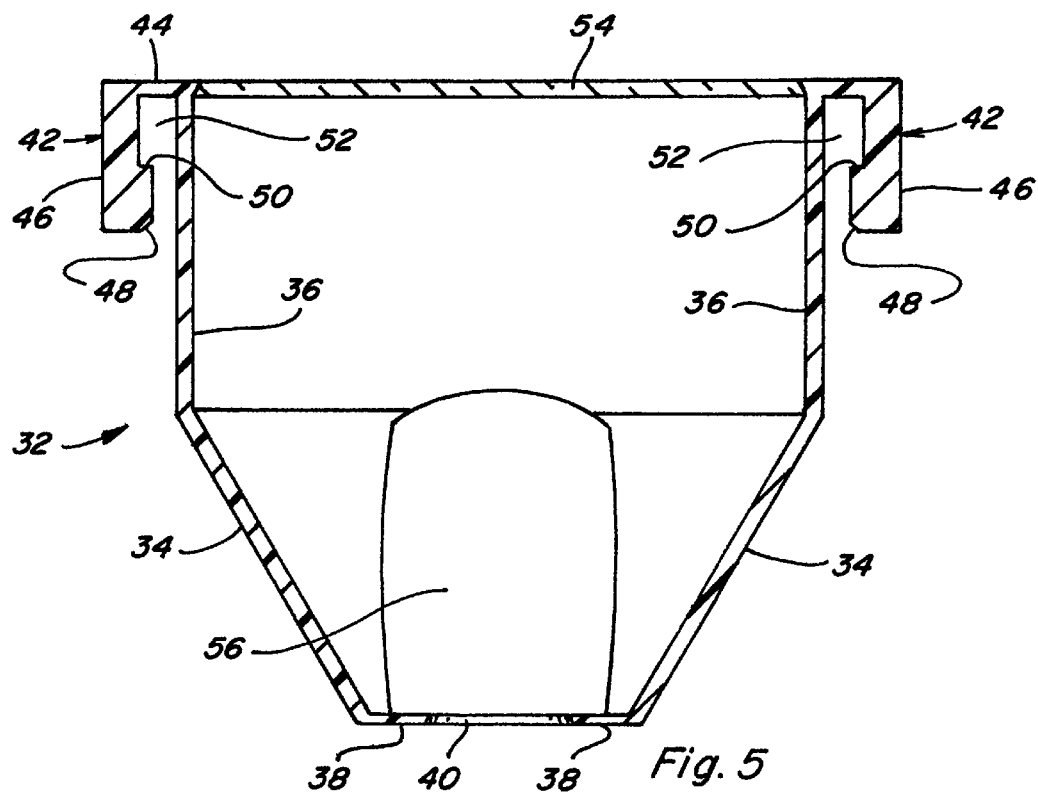
FIG. 5 is a cross-sectional view of the inner member illustrated in FIG. 1.
Figure 4:
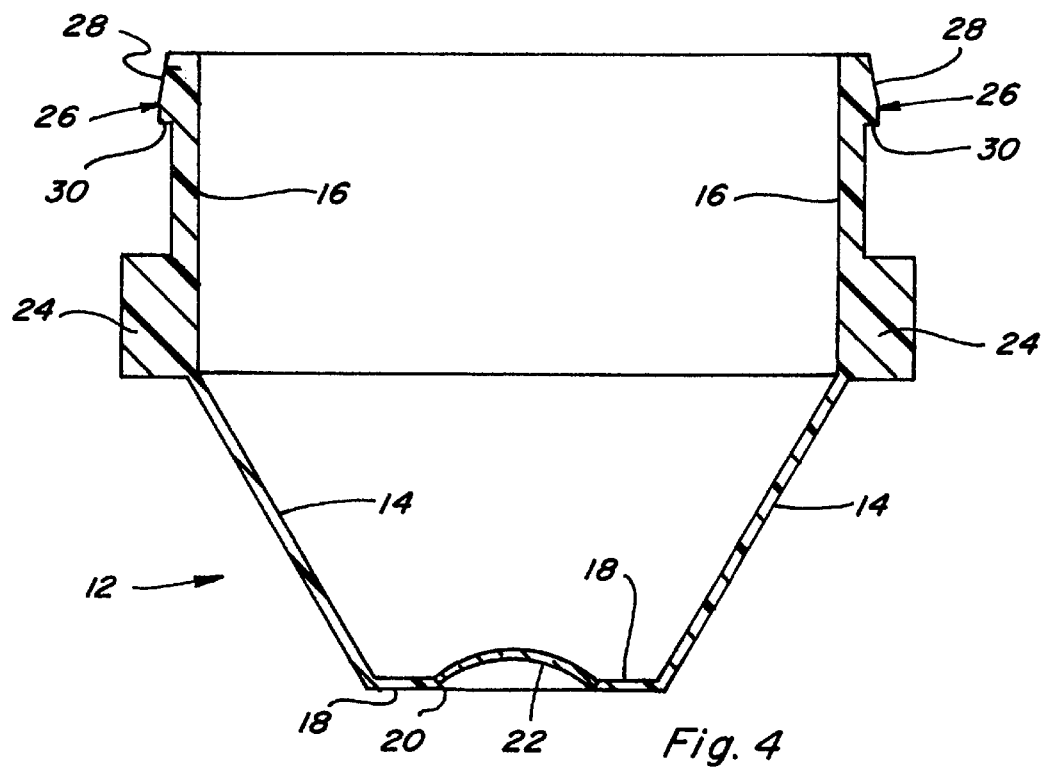
FIG. 4 is a cross-sectional view of the outer member illustrated in FIG. 1.

Referring to the drawings more particularly by reference numerals wherein like numerals refer to like parts, number 10 in FIGS. 1, 2 and 3 identifies one embodiment of a rotatable diagnostic or treatment lens constructed according to the teachings of the present invention. The lens assembly 10 includes an outer member 12 as best shown in FIG. 4 and an inner member 32 as best shown in FIG. 5, which members, in combination, define the overall lens assembly 10. The members 12 and 32 are cooperatively engageable with each other as will be hereinafter explained such that the inner member 32 is selectively rotatable within the outer member 12.

As best shown in FIG. 4, the outer member 12 is substantially hollow and is defined by annular wall portions 14 and 16. In the preferred embodiment, wall portion 14 is substantially frusto-conical in shape and includes an annular end wall portion 18 adjacent one end portion thereof defining an opening 20 therethrough into which a fixed central lens 22 is mounted. The central lens 22 is generally concave in shape as illustrated in FIGS. 1, 2 and 4 and can be either fixedly mounted or removably attached to end wall portion 18 by means well known in the art. Central lens 22 is positioned adjacent to a patient's eye and is utilized to view and assess the posterior 30° of the retina including the disc, arcades and macula. A plurality of mirrors 56, 58 and 60 positioned adjacent the central viewing lens 22 as will be hereinafter explained are utilized in conjunction with central lens 22 to view other interior portions of the eye including, but not limited to, the irido-corneal angle and peripheral portions of the vitreous chamber and the retina. The concavity of the central lens 22 allows for magnification of the interior structure of the eye, especially the irido-corneal angle and the retina, and although the lens 22 is generally of a circular construction, other shapes and configurations including a substantially flat shape may likewise be utilized. In addition, the central lens 22 can be either clear or colored, also known as filtered, depending upon how the lens device 10 is to be utilized.

The wall portion 16 of outer member 12 is substantially cylindrical in shape (FIG. 4) and, in the preferred embodiment, is integrally formed with wall portion 14. It is also recognized and anticipated that wall portions 14 and 16 can be constructed so as to be removably attached to one another. Wall portion 16 further includes an optional annular protrusion 24, as well as an outwardly extending annular lip or flange portion 26 located adjacent the upper end portion thereof as best illustrated in FIGS. 1 and 4. The annular flange or lip portion 26 includes an outer beveled or tapered surface 28 and a seating or shoulder surface 30 as best shown in FIG. 4. The optional protrusion 24 can be positioned and located anywhere on wall portion 16, or even on wall portion 14, so as to allow a user to more easily hold the device 10 in a fixed position adjacent a patient's eye. Preferably, protrusion 24 is a continuous annular ring member integrally formed with outer member 12, although other constructions can likewise be utilized including a construction where protrusion 24 does not extend continuously around outer member 12 but instead includes one or more of a plurality of protrusions or projections spaced around the periphery of outer member 12.

The inner member 32 is substantially similar in overall shape to outer member 12 and includes corresponding mating wall portions 34 and 36. Like wall portion 14, wall portion 34 is likewise substantially frusto-conical in shape and includes an annular end wall portion 38 defining an opening 40 therethrough. The opening 40 is shaped and dimensioned so as to enable at least a portion of the central viewing lens 22 to extend therethrough as best shown in FIG. 1. In similar fashion, wall portion 36, like wall portion 16, is substantially cylindrical in shape and preferably is integrally formed with wall portion 34. Here again, it is recognized and anticipated that wall portions 34 and 36 can likewise be constructed so as to be removably attached to one another. In order to achieve a rotatable connection between the inner and outer members 32 and 12 respectively, wall portion 36 preferably further includes an overhanging peripheral annular portion 42 which is constructed to slidably engage the annular flange 26 associated with outer member 12 so as to hold the members 12 and 32 in an engaged rotatable relationship as will be explained. In this regard, it is recognized and anticipated that any construction can be used to achieve the rotatable connection between inner and outer members 32 and 12.

More particularly, overhanging peripheral annular portion 42 includes a top edge portion 44 and a downturned wall or flange portion 46 located adjacent the upper end portion of wall portion 36 as best illustrated in FIG. 5. Again, it is preferred that the annular portion 42 be integrally formed with wall portion 36, although other constructional arrangements for fixedly attaching annular portion 42 to wall portion 36 are also contemplated. The annular downturned flange portion 46 includes an optional annular beveled edge portion 48 and a shoulder surface 50. Importantly, the overhanging annular portion 42 defines an annular channel 52 adjacent wall portion 36, the channel 52 being shaped and dimensioned so as to cooperatively receive the annular flange or lip portion 26 associated with outer member 12. A transparent planar viewing member 54 is fixedly secured adjacent the top edge portion of wall portion 36 as shown in FIGS. 1 and 5, the member 54 being made of glass or some other suitable viewing material. In this regard, the member 54 can be either clear or filtered depending upon the particular use of the device 10 as some laser applications require a filtered viewing member 54.

Inner member 32 also importantly includes a plurality of mirrors such as the mirrors 56, 58 and 60 illustrated in FIGS. 1, 2 and 5. Although any plurality of mirrors can be associated with the inner member 32, including the use of a single mirror, for illustrative purposes only, the present construction will be described and disclosed with respect to a three mirror arrangement similar to the mirror arrangement associated with known three mirror fundus contact lenses presently in use. In this regard, the mirrors 56, 58 and 60 are circumferentially spaced adjacent annular end portion 38 such that the mirrors are angularly inclined relative to the vertical adjacent the central lens 22 when the inner member 32 is cooperatively engaged with the outer member 12 as best shown in FIG. 2. In the case of the three mirrors illustrated in FIG. 2, such mirrors are circumferentially spaced 120° apart and are mounted at different angles of inclination relative to the frusto-conical shaped wall portion 34 so as to allow the irido-corneal angle and different areas of the retina or other portions of the eye to be evaluated. As previously explained, typically, the mirrors 56, 58 and 60 are inclined at angles such as 59°, 67° and 73° relative to the vertical such that each respective mirror will reflect light at a different angle so that different parts of the eye can be examined. In the case of the known three mirror fundus contact lens, manufactures of these types of lenses have universally assigned different sizes and shapes to each such mirror so that users can quickly and easily identify each mirror and its associated angular inclination. The means for mounting the respective mirrors within the inner member 32 are well known in the art and any suitable means can be utilized to accomplish this task.

It is recognized and anticipated that any number of mirrors, including a single mirror, can be positioned or oriented within the inner member 32 based upon the overall size and shape of the member 32, the size and shape of the respective mirrors, and based upon the particular application desired. Besides the known sizes and shapes already assigned to some mirrors, it is likewise recognized and anticipated that the size and shape of each respective mirror can be varied as well as the particular angle of inclination associated with each respective mirror and the spacing between respective mirrors. The mirrors 56, 58 and 60 can likewise be oriented and mounted within inner member 32 in a wide variety of other configurations and arrangements other than those disclosed in FIGS. 1, 2 and 3 without departing from the spirit and scope of the present invention. In addition, the present device 10 can likewise operate with a single mirror as will be hereinafter explained.

Inner member 32 is cooperatively engageable with outer member 12 by insertably positioning member 32 within member 12 such that the annular flange or lip portion 26 associated with outer member 12 is insertably received within the annular channel 52 associated with inner member 32. In this regard, the size and shape of the respective wall portions associated with members 12 and 32 are such that members 12 and 32 are compatible for cooperative mating engagement with each other as best shown in FIG. 1. When inner member 32 is inserted within outer member 12, the beveled edge portion 48 slides along beveled edge portion 28 until the seating surface 30 of member 12 rests upon the shoulder surface 50 associated with member 32. When so positioned, the mating surfaces 30 and 50 prevent inner member 32 from being insertably removed from member 12 and, importantly, at the same time, inner member 32 is rotatably movable relative to outer member 12. Rotation of inner member 32 is accomplished by simply holding the outer member 12 stationary such as by gripping the same adjacent annular protrusion 24 and thereafter rotating the overhanging annular portion 42 so as to properly align and orient the appropriate mirror at the appropriate location opposite the area of the retina or other eye portion to be evaluated. A user can simply rotate the peripheral annular portion 42 with the forefinger so that the selected mirror is properly positioned without physically moving the outer member 12 against the eye of the patient. This rotation can be easily accomplished with one hand. In this regard, it is recognized that the frictional engagement of annular portions 26 and 42 should be such that shoulder surface 50 can be easily rotated 360° relative to its mating or seating surface 30.

Figure 6:
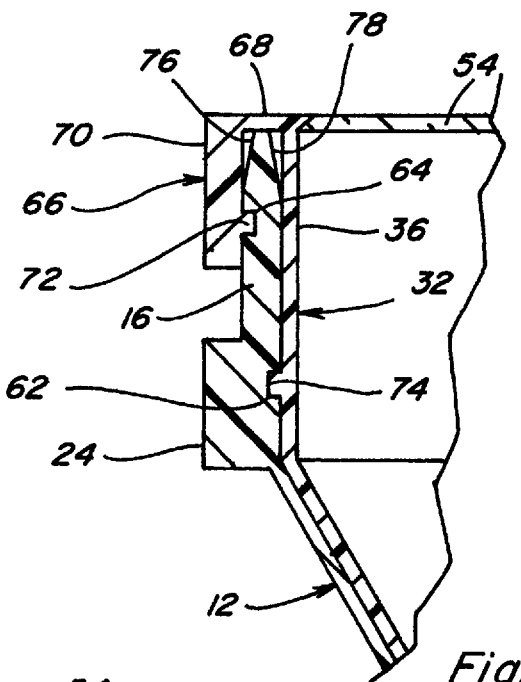
FIG. 6 is a partial cross-sectional view showing an alternative embodiment for rotatably connecting the inner and outer members.

FIG. 6 discloses another engagement arrangement between members 12 and 32 for achieving 360° rotatability of inner member 32 relative to outer member 12. In the embodiment illustrated in FIG. 6, the wall portion 16 of outer member 12 includes a pair of recesses 62 and 64, recess 62 being located in the area of annular protrusion 24 and facing inwardly towards inner member 32 whereas recess 64 is located towards the upper end portion of wall portion 16 and faces outwardly away from inner member 32. In corresponding fashion, inner member 32 includes an overhanging annular portion 66 which likewise includes a top edge portion 68 and a downwardly extending annular flange portion 70. Like annular portion 42, annular portion 70 defines a channel by and between wall portion 36 and annular flange portion 70, annular flange portion 70 also including a projection 72 which is sized and shaped for cooperative engagement with recess 64. In similar fashion, wall portion 36 likewise includes an outwardly extending projection 74 which is sized and shaped for cooperative engagement with recess 62. When the inner member 32 is insertably positioned within outer member 12, the projections 72 and 74 will slidably move along the respective inner and outer surfaces of wall portion 16 until such projections are cooperatively engaged with their corresponding recesses 62 and 64. To aid in this engagement, the terminal end portion of wall portion 16 may include beveled or tapered surfaces 76 and 78 on each opposite side thereof. Once so engaged, the recesses 62 and 64 and their corresponding projections 72 and 74 not only prevent inner member 32 from being inadvertently separated from outer member 12, but such male/female connection means also enable the inner member 32 to be freely rotated 360° relative to outer member 12. In all other respects, the inner and outer members illustrated in FIG. 6 are substantially similar in construction and operation to the members 12 and 32 previously described with respect to FIGS. 1–5.

Figure 7:
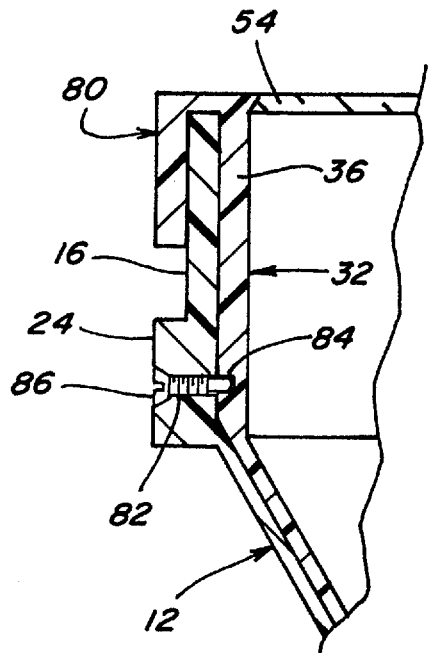
FIG. 7 is a partial cross-sectional view showing still another embodiment for rotatably connecting the inner and outer members.

FIG. 7 illustrates still another constructional arrangement for rotatably engaging inner member 32 to outer member 12. In this particular embodiment, the upper end portion of wall portion 16 is cooperatively received within the channel formed by the overhanging annular portion 80 associated with inner member 32. In addition, an opening or aperture 82 extends completely through the annular protrusion 24 associated with outer member 12 and a corresponding groove or recess 84 is positioned and located on wall portion 36 in communication with opening 82 when the members 12 and 32 are engaged with each other as previously explained. A partially threaded pin member 86 is thereafter inserted within the opening 82 such that its terminal end portion extends into the groove or recess 84 formed within wall portion 36. When so engaged, the pin member 86 will prohibit up and down movement of inner member 32 relative to outer member 12 and, at the same time, will allow rotational movement of inner member 32 relative to outer member 12 as previously explained. In this particular embodiment, it is recognized and anticipated that the opening 82, the recess 84, and pin member 86 can be positioned and located on other portions of the outer and inner members 12 and 32 so long as the inner member 32 is freely rotatable within outer member 12 and that separation of such members is prohibited. It is also recognized and anticipated that any number of pin members 86 can be utilized around the periphery of the outer and inner members 12 and 32 and it is also recognized and anticipated that a wide variety of other male/female connection means may be utilized in association with the outer and inner members 12 and 32 without departing from the spirit and scope of the present invention.

Although the various embodiments of the present lens device are particularly adaptable for use in association with a wide variety of diagnostic type lenses such as gonioscopy and fundoscopic lenses, the present invention is likewise equally adaptable for use in many other eye lens applications including other types of ophthalmological lenses as well as lenses used in laser treatment and/or surgery of the eye. In this regard, regardless of the specific use, the present devices can be used in association with any of a variety of standard diagnostic or treatment procedures that involve the use of a diagnostic or treatment type ocular lens and the shape and diameter of the central lens 22 can be varied depending upon the specific use or application of such devices.

Figure 8:
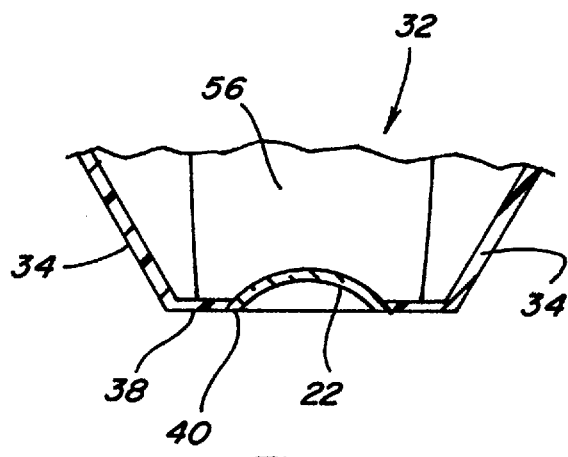
FIG. 8 is a partial cross-sectional view showing still another embodiment of the present lens device.

In addition, the outer and inner members 12 and 32 can be made from a wide variety of different types of materials including metal, metal alloys and plastics as well as any various combinations of such materials. Additionally, the central viewing lens 22 can likewise be associated with the inner member 32 as illustrated in FIG. 8 and such lens can likewise rotate with the mirrors without departing from the spirit and scope of the present invention. Still further, the overall shape and dimensions of the respective inner and outer members can be varied to accommodate different applications. For example, the outer and inner members 12 and 32 can be entirely frusto-conical in shape, entirely cylindrical in shape, or such members may take on a wide variety of other shapes and configurations so long as the plurality of mirrors associated therewith can be fixedly mounted within the inner member at their proper angular orientations, so long as the inner member is rotatable relative to the outer member, and so long as the central viewing lens 22 can be effectively positioned adjacent a patient's eye.

Importantly, it is also recognized and anticipated that the construction and location of the mating surfaces 30 and 50, the male and female connections 62, 64, 72 and 74 and the wall and flange portions 16, 26, 36, 42, 66 and 80 can all be reversed so that those portions located on member 12 can be located on member 32 and vice versa without departing from the spirit and scope of the present invention so long as inner member 32 is rotatable relative to outer member 12.

Although it is preferred that the present lens devices include a plurality of mirrors because such inclusion increases the usefulness and efficiency of the present devices, it is also recognized and contemplated that the present devices can likewise function with a single mirror. In this situation, the single mirror can be selectively positioned relative to the periphery of the central lens 22 at any location therearound so as to properly orient the single mirror relative to lens 22 to view a particular portion of the eye. In addition, although it is preferred that inner member 32 rotate a full 360° relative to outer member 12, it is likewise recognized and anticipated that the construction of outer and inner members 12 and 32 can be such that the rotatable mounting of inner member 32 within outer member 12 will provide for an operative range of rotation for inner member 32 of less than 360°. In this regard, the range of rotation of inner member 32 relative to outer member 12 can vary depending upon the specific use or application of the present devices.

Thus there has been shown and described several embodiments of a novel rotatable diagnostic and/or treatment lens device for use in examining and evaluating the irido-corneal, retina and other portions of the eye, which devices fulfill all of the objects and advantages sought therefor. Many changes, modifications, variations and other uses and applications of the present constructions will, however, become apparent to those skilled in the art after considering this specification and the accompanying drawings. All such changes, modifications, variations and other uses and applications which do not depart from the spirit and scope of the invention are deemed to be covered by the invention which is limited only by the claims which follow.

What is claimed is:

1. A lens device for examining portions of the human eye comprising an inner and an outer member each having opposed end portions and associated wall means, said outer member having a viewing lens positioned adjacent one end portion thereof, said inner member being rotatably mountable within said outer member and having at least one mirror associated therewith, said at least one mirror being located adjacent said viewing lens when said inner member is mounted within said outer member, said inner member being rotatably movable relative to said outer member such that said at least one mirror is selectively positionable relative to said viewing lens.

2. The lens device defined in claim 1 wherein said inner member has a transparent planar viewing member associated with one end portion thereof.

3. The lens device defined in claim 1 including a plurality of mirrors associated with said inner member.

4. The lens device defined in claim 3 wherein each of said plurality of mirrors is positioned and located within said inner member at a different angle of inclination relative to the vertical.

5. The lens device defined in claim 3 wherein said plurality of mirrors are positioned and located so as to be circumferentially spaced around said viewing lens when said inner member is mounted within said outer member.

6. The lens device defined in claim 1 wherein said outer member includes a frusto-conical shaped portion.

7. The lens device defined in claim 1 wherein said inner member includes a frusto-conical shaped portion.

8. The lens device defined in claim 1 wherein said outer member includes a cylindrical portion.

9. The lens device defined in claim 1 wherein said inner member includes a cylindrical portion.

10. The lens device defined in claim 1 wherein said viewing lens is generally concaved in shape.

11. The lens device defined in claim 1 wherein said inner member is rotatable a full 360°.

12. The lens device defined in claim 1 wherein one end portion of said inner member includes an overhanging peripheral portion.

13. The lens device defined in claim 12 wherein the wall means associated with said outer member includes a protrusion extending outwardly away from said inner member, said protrusion being shaped and dimensioned so as to enable a user to fixedly hold said outer member in a stationary position adjacent a patient's eye while said inner member is rotated relative thereto, said inner member being rotated by rotating said overhanging peripheral portion.

14. A lens device for examining portions of the human eye comprising inner and outer members each having opposed end portions and associated wall means, said inner member being rotatably positionable within said outer member and having a viewing lens positioned adjacent one end portion thereof, said inner member further including at least one mirror positioned and located adjacent said viewing lens, said inner member being rotatably movable relative to said outer member such that said at least one mirror is selectively positionable relative to a portion of the human eye to be examined.

15. The lens device defined in claim 14 wherein said inner member is rotatable a full 360°.

16. The lens device defined in claim 14 including a plurality of mirrors associated with said inner member, each of said plurality of mirrors being circumferentially positioned and located adjacent said viewing lens at a different angle of inclination relative to the vertical.

17. A lens device for examining portions of the human eye comprising an outer member having opposed top and bottom end portions and associated wall means, said outer member having a viewing lens positioned and located adjacent its bottom end portion, an inner member having opposed top and bottom end portions and associated wall means, said inner member being positionable within said outer member and including at least one mirror positioned and located adjacent its bottom end portion, said at least one mirror being located proximally to said viewing lens when said inner member is positioned within said outer member, an overhanging peripheral portion associated with the top end portion of said inner member, said overhanging peripheral portion being cooperatively engageable with the top end portion of said outer member when said inner member is positioned within said outer member such that a rotatable connection is formed therebetween, said inner member being rotatably movable relative to said outer member such that said at least one mirror can be selectively positioned relative to said viewing lens.

18. The lens device defined in claim 17 wherein the top end portion of said outer member includes an outwardly extending shoulder portion, the overhanging peripheral portion of said inner member including a corresponding shoulder portion and defining a channel adjacent said associated wall means, said channel being shaped and dimensioned so as to cooperatively receive the top end portion of said outer member such that the shoulder portion associated with said outer member mates with and rests upon the shoulder portion associated with said inner member.

19. The lens device defined in claim 17 wherein the top end portion of said outer member includes a pair of recesses, and wherein the wall means and the overhanging peripheral portion of said inner member each include a corresponding projection, said projections being cooperatively received within said corresponding recesses when the top end portion of said outer member is cooperatively engaged with the overhanging peripheral portion of said inner member.

20. The lens device defined in claim 19 wherein the wall means associated with said outer member includes inner and outer surfaces, one of said pair of recesses being positioned and located on the outer surface of said associated wall means and one of said pair of recesses being positioned and located on the inner surface of said associated wall means.

21. The lens device defined in claim 17 including a plurality of mirrors positioned and located adjacent the bottom end portion of said inner member, each of said plurality of mirrors being positioned and located within said inner member at a different angle of inclination relative to the vertical.

22. A lens device for examining portions of the human eye comprising an outer member having opposed top and bottom end portions and associated wall means, said outer member having a viewing lens positioned and located adjacent its bottom end portion, an inner member having opposed top and bottom end portions and associated wall means, said inner member being positionable within said outer member and including at least one mirror positioned and located adjacent its bottom end portion, said at least one mirror being located proximally to said viewing lens when said inner member is positioned within said outer member, an overhanging peripheral portion associated with the top end portion of said inner member defining a channel adjacent said associated wall means, the top end portion of said outer member being cooperatively received within said channel, a first opening extending through the wall means associated with said outer member, a second opening extending at least partially through the wall means associated with said inner member, and a pin member insertably receivable within said first and second openings when said inner member is positioned within said outer member, said inner member being rotatably movable relative to said outer member such that said at least one mirror can be selectively positioned relative to said viewing lens.

23. The lens device defined in claim 22 including a plurality of openings extending through the wall means associated with said outer member, a corresponding plurality of openings extending at least partially through the wall means associated with said inner member, and a plurality of pin members insertably receivable within the respective openings associated with said outer and inner members when said inner member is positioned within said outer member.

* * * * *